United States Patent
Shirahata et al.

(10) Patent No.: US 9,029,609 B2
(45) Date of Patent: May 12, 2015

(54) PHENOL PURIFICATION PROCESS

(71) Applicant: Mitsui Chemicals, Inc., Tokyo (JP)

(72) Inventors: Tatsuo Shirahata, Ichihara (JP);
Masahiro Hatakeyama, Ichihara (JP);
Kozo Yasuda, Chiba (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 14/391,636

(22) PCT Filed: Apr. 11, 2013

(86) PCT No.: PCT/JP2013/060899
§ 371 (c)(1),
(2) Date: Oct. 9, 2014

(87) PCT Pub. No.: WO2013/154147
PCT Pub. Date: Oct. 17, 2013

(65) Prior Publication Data
US 2015/0065755 A1  Mar. 5, 2015

(30) Foreign Application Priority Data
Apr. 13, 2012 (JP) ................................. 2012-091712

(51) Int. Cl.
*C07C 37/74* (2006.01)
*C07C 37/68* (2006.01)

(52) U.S. Cl.
CPC .............. *C07C 37/74* (2013.01); *C07C 37/685* (2013.01)

(58) Field of Classification Search
CPC ............................. C07C 37/685; C07C 37/74
See application file for complete search history.

(56) References Cited

U.S. PATENT DOCUMENTS

| | | | |
|---|---|---|---|
| 2,346,664 A * | 4/1944 | Corson | 568/758 |
| 3,029,293 A * | 4/1962 | Nixon, Jr. | 568/754 |
| 3,150,191 A | 9/1964 | Oldenburg | |
| 5,245,090 A | 9/1993 | Schutz et al. | |
| 5,264,636 A * | 11/1993 | Shirahata et al. | 568/754 |
| 2003/0163007 A1 | 8/2003 | Fulmer et al. | |

FOREIGN PATENT DOCUMENTS

| | | | |
|---|---|---|---|
| GB | 920864 | * | 3/1963 |
| GB | 1231991 A | | 5/1971 |
| JP | 3711664 | | 8/1962 |
| JP | 4212250 | | 7/1967 |
| JP | 541289 | | 1/1979 |
| JP | 6192151 | | 7/1994 |
| JP | 2005526718 T2 | | 9/2005 |
| WO | 2006087943 A1 | | 8/2006 |
| WO | 2009063763 A1 | | 5/2009 |

OTHER PUBLICATIONS

International Search Report dated Jun. 25, 2013 filed in PCT/JP2013/060899.
CSJ, The Chemical Society of Japan, Jikken Kagaku Kozo 17, 2nd edition, 2nd print, Maruzen Co., Ltd., 1956, pp. 340-341; Cited in International Search Report.

* cited by examiner

*Primary Examiner* — Brian J Davis
(74) *Attorney, Agent, or Firm* — Rankin, Hill & Clark LLP

(57) ABSTRACT

The present invention provides an easy process for purifying phenol by separating carbonyl compounds through selective hydrogenation of the compounds to the corresponding alcohols then distillation. The phenol purification process of the present invention comprises bringing phenol into contact with a copper-based catalyst in the presence of hydrogen to convert carbonyl compounds contained in the phenol to the corresponding alcohol compounds, and separating the alcohol compounds and phenol by distillation.

12 Claims, 1 Drawing Sheet

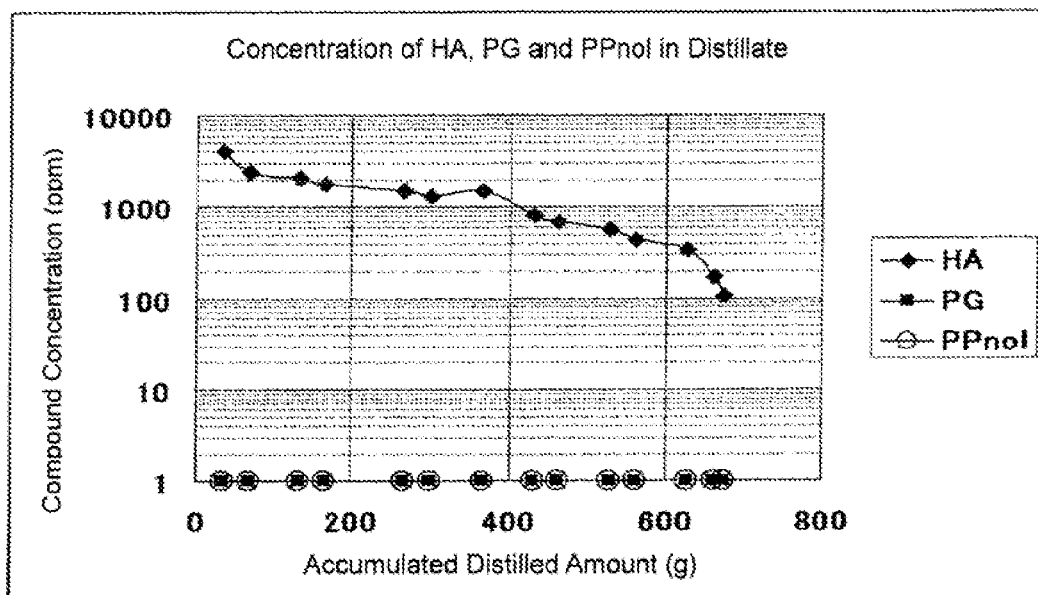

PHENOL PURIFICATION PROCESS

TECHNICAL FIELD

The present invention relates to a phenol purification process, and particularly a process for purifying a phenol resultant by cumene method.

BACKGROUND ART

Phenol is produced through a step of oxidizing alkylbenzene to alkylaryl hydroperoxide, a step of concentrating an oxidation reaction product of alkylbenzene, a step of subjecting the concentrated solution to cleavage into phenol and a ketone with an acid catalyst, a step of neutralizing the acid cleavage product, and a step of separating the acid cleavage product by distillation.

As a process for producing phenol, for example, a process for acid decomposition of cumene hydroperoxide obtained by oxidation of cumene is well known. The acid decomposition product in this process contains, in addition to phenol and acetone as main components, various by-products such as α-methylstyrene, acetophenone, cumylphenol, 2-phenyl-2-propanol (also called α-dimethylphenyl carbinol) and unreacted cumene, and various carbonyl compounds such as a trace amount of hydroxyacetone (HA) and α-phenylpropionaldehyde (α-PPA). In the application of phenol, an example of which is polycarbonate manufactured from diphenylolpropane (also called bisphenol A) as a raw material, high-purity phenol is required.

For such a high purity phenol, it is necessary that the content of hydroxyacetone (HA) as an impurity is reduced to 30 ppm or less, preferably 10 ppm or less. In addition, it is necessary that the total amount of other aliphatic and aromatic carbonyl compounds contained, i.e., total amount of carbonyl compounds other than HA, is reduced to 100 ppm or less, preferably 50 ppm or less. In order to obtain such a high-purity phenol, purification is carried out, wherein most of the low-boiling substances such as acetone, cumene, water and α-methylstyrene, and most of the high-boiling substances such as acetophenone and 2-phenyl-2-propanol are removed from a neutralization product of the acid decomposition product by means of fractional distillation to give a phenol fraction, and further the aliphatic carbonyl compounds such as hydroxyacetone, and the aromatic carbonyl compounds such as α-phenylpropionaldehyde are removed from the phenol fraction. However, it is particularly difficult to remove those carbonyl compounds from phenol, which thus deteriorates the quality of phenol as a product.

For a conventional process for producing high-purity phenol, for example, JP-B No. 37-11664 (Patent Document 1) proposes a process in which hydroxyacetone and phenol are subjected to react by bringing crude phenol (content of hydroxyacetone: 200 ppm) into contact with an activated alumina catalyst at 360° C. to give 2-methylbenzofuran (2-MBF), and phenol and 2-methylbenzofuran are then separated by means of steam distillation. In addition, JP-B No. 54-1289 (Patent Document 2) discloses a process in which activated alumina is used for the purification of cresol. In addition, JP-B No. 42-12250 (Patent Document 3) proposes a process which comprises bringing crude phenol into contact with a silica/alumina catalyst at 150 to 250° C. to convert carbonyl compound as an impurity to another compound, and separating the compound and phenol by distillation. Moreover, GB Patent No. 1231991 (Patent Document 4) proposes a process which comprises bringing crude phenol containing no water into contact with an acidic ion exchange resin catalyst at 80 to 150° C. to convert carbonyl compound as an impurity to another compound, and then separating the compound and phenol by distillation.

However, the above methods cause a problem such that the efficiency of the removal of impurities is insufficient, or that phenol and α-methylstyrene, which are useful components in the crude phenol, react with impurities, or each of them undergoes addition reaction with the other or independently to produce cumylphenol or olefin dimers, and thus the useful components are lost.

CITATION LIST

Patent Document

[Patent Document 1] JP-B No. 37-11664
[Patent Document 2] JP-B No. 54-1289
[Patent Document 3] JP-B No. 42-12250
[Patent Document 4] GB Patent No. 1231991

SUMMARY OF THE INVENTION

Technical Problem

It is an object of the present invention to provide a phenol purification process capable of producing high-purity phenol, comprising selectively hydrogenating target carbonyl compounds to convert the carbonyl compounds to the corresponding alcohol compounds without causing the loss of the useful components mentioned above, and separating the alcohol compounds and phenol by distillation.

Technical Solution

The present inventors have made their earnest studies to overcome the above problem and have found that by using a copper-based catalyst to selectively hydrogenate carbonyl compounds contained as impurities in phenol to convert the carbonyl compounds to the corresponding alcohol compounds, the above problem can be overcome, thereby completing the present invention.

That is, the present invention is summarized as a phenol purification process comprising bringing phenol into contact with a copper-based catalyst in the presence of hydrogen to convert aliphatic carbonyl compounds and aromatic carbonyl compounds contained in the phenol to corresponding alcohol compounds, and separating the alcohol compounds and phenol by distillation. Hereinafter, phenol containing impurities such as carbonyl compounds is also referred to as "crude phenol", and phenol from which impurities such as carbonyl compounds have been removed is also referred to as "high-purity phenol".

The copper-based catalyst comprises at least one of copper and copper oxide (A) and oxide(s) of at least one element selected from silicon, aluminum, zinc, chromium, barium and manganese (B).

The weight ratio of at least one of copper and copper oxide (A) to oxide(s) of at least one element selected from silicon, aluminum, zinc, chromium, barium and manganese (B), both of which constitute the cooper-based catalyst, (A)/(B), is in the range of from 9/1 to 1/9. The catalytic hydrogenation is performed desirably at a reaction temperature of 50 to 300° C. at a hydrogen pressure of 0.5 to 30 MPa.

Advantageous Effects of the Invention

According to the present invention, by using a copper-based catalyst such as a catalyst comprising at least one of copper and copper oxide (A) and oxide(s) at least one element selected from silicon, aluminum, zinc, chromium, barium and manganese (B) to hydrogenate carbonyl compounds contained in crude phenol to convert the carbonyl compounds to the corresponding alcohol compounds, it is possible to easily separate phenol by distillation to produce high-purity phenol, while inhibiting the loss of phenol and α-methylstyrene, which are useful components in the crude phenol. Thus, the purification process of the present invention is industrially of significant value.

BRIEF DESCRIPTION OF DRAWING

FIG. 1 is a figure showing the test result of distillation of hydroxyacetone (HA), a hydrogenated product of hydroxyacetone, i.e. propylene glycol (PG), a hydrogenated product of α-phenylpropionaldehyde (α-PPA), i.e., 2-phenyl-1-propanol (PPnol), and phenol (See Reference Example 1).

DESCRIPTION OF EMBODIMENTS

The phenol to be purified in the present invention is a residue obtained by removing light fractions (for example, most part of acetone, cumene and α-methylstyrene) by fractional distillation of a neutralized product of acid-decomposed product obtained by acid-decomposing cumene hydroperoxide obtained from the oxidation reaction of cumene, and its composition is as follows. This compositional range is set forth just in order to give an example, and not to limit the technical scope of the present invention.

Phenol 87.0 to 95.6 wt %
Cumene 1.0 to 0.1 wt %
α-methylstyrene 2.0 to 0.1 wt %
Hydroxyacetone 0.5 to 0.1 wt %
α-phenylpropionaldehyde 0.5 to 0.1 wt %
Acetophenone 4.0 to 2.0 wt %
2-phenyl-2-propanol 1.0 to 0.5 wt %
Other high-boiling components 4.0 to 1.5 wt %

In the above phenol fraction, separating cumene and α-methylstyrene as light fractions, and acetophenone, 2-phenyl-2-propanol and other high-boiling components as heavy fractions from phenol is relatively easy by distillation. However, separating carbonyl compounds such as hydroxyacetone and α-phenylpropionaldehyde from phenol by distillation is difficult. In the present invention, such carbonyl compounds are converted, by hydrogenation reaction using a specific catalyst, to the corresponding alcohols, and the corresponding alcohols are removed by distillation. This characterizes the phenol purification process of the present invention. A phenol preferred in the purification process of the present invention is phenol containing carbonyl compound as an impurity wherein the carbonyl compound is at least one compound selected from aromatic carbonyl compounds and aliphatic carbonyl compounds, and more specifically, phenol containing, as an impurity, hydroxyacetone (HA) as an aliphatic carbonyl compound, and/or α-phenylpropionaldehyde (α-PPA) as an aromatic carbonyl compound. The particularly preferred phenol is phenol containing not more than 1 wt % of hydroxyacetone (HA). In the hydrogenation reaction according to the present invention, HA is converted to propylene glycol (PG), and α-PPA is converted to 2-phenyl-1-propanol (PPnol).

The copper-based catalyst used as the catalytic hydrogenation catalyst in the present invention is usually a catalyst comprising at least one of copper and copper oxide (A), preferably a catalyst comprising at least one of copper and copper oxide (A) and oxide(s) of at least one element selected from silicon, aluminum, zinc, chromium, barium and manganese (B). The copper-based catalyst is more preferably a catalyst consisting of at least one of copper and copper oxide (A) and oxide(s) of at least one element selected from silicon, aluminum, zinc, chromium, barium and manganese (B); and is particularly preferably a catalyst consisting of at least one of copper and copper oxide (A) and oxide (s) of at least one element selected from silicon, zinc, chromium, barium and manganese.

The method for preparing the copper-based catalyst is not particularly limited, and an exemplary method thereof is as follows. That is, the catalyst used in the present invention can be prepared by using, as raw materials, at least one kind selected from a nitrate, a sulfate, a carbonate, an acetate, a chloride, an oxide, a hydroxide and the like of copper, aluminum, zinc, chromium, barium and manganese, and further at least one kind selected from a silicate (for example, sodium silicate, potassium silicate), an alkoxide compound of silicon (for example, tetramethoxysilane, tetraethoxysilane), a halogen compound of silicon (tetrachlorosilane, tetrabromosilane) and the like, by known method such as co-precipitation method, immersion method and kneading method.

Here, in the catalyst used in the present invention, the weight ratio of at least one of copper and copper oxide (A) to oxide(s) of at least one element selected from silicon, aluminum, zinc, chromium, barium and manganese (B), [(A)/(B)], is not particularly limited, but is desirably in the range of from 9/1 to 1/9, particularly desirably in the range of from 4/1 to 1/4.

A catalyst included in the catalyst used in the present invention, i.e., the catalyst comprising at least one of copper and copper oxide (A) and oxide(s) of at least one element selected from silicon, aluminum, zinc, chromium, barium and manganese (B) may be a catalyst prepared by the known methods described above, such as co-precipitation method, immersion method and kneading method, or a commercially available catalyst (for example, E35S manufactured by JGC Catalysts and Chemicals Ltd., and G-22 and G-99 manufactured by Sud Chemie Catalyst).

The shape of the catalyst used in the present invention is not particularly limited, but the catalyst is desirably a tablet-shaped or a noodle-shaped. These shapes are easily available industrially. The size of the catalyst used in the present invention is determined according to the inner diameter of a reactor column employed, but the catalyst having a diameter of 2 to 6 mm and a height of 2 to 6 mm is preferable.

Examples of a reactor for performing the purification process of the present invention are a batch-type reactor, a fixed-bed continuous reactor, a fluidized-bed continuous reactor and a moving-bed continuous reactor. The use of a fixed-bed continuous reactor, which equipment is simple, is desirable.

In order to control rapid heat generation when hydrogenation reaction is initiated and to allow the catalyst to effectively exhibit its activity, it is effective that the copper-based catalyst used in the present invention is subjected to preliminary reduction treatment in accordance with an ordinary method. In general, this reduction treatment is performed by bringing the catalyst into contact with a hydrogen gas at 100 to 300° C.

The hydrogenation reaction temperature is usually 50 to 300° C., preferably 80 to 200° C.

The reaction pressure is generally a hydrogen pressure of 0.5 to 30 MPa, preferably 1 to 10 MPa. The reaction time, in the case of batch reaction, is usually 1 to 20 hours. In the case of continuous-type reaction, the feeding rate (LHSV) of the crude phenol per unit volume of the solid catalyst in the reaction is desirably 0.5 hr$^{-1}$ to 20 hr$^{-1}$, more desirably 1 hr$^{-1}$ to 10 hr$^{-1}$.

When a continuous reactor is used in the present invention, the reactor employed may be composed of a single reactor, or a plurality of reactors. Particularly, when the reactor is composed of a plurality of reactors, reaction conditions can be controlled with greater precision by serially arranging the reactors.

In the present invention, carrying out a known purification method, such as a purification procedure using an acidic ion exchange resin, after or before performing the reaction of converting carbonyl compound to alcohol in the presence of hydrogen, does not limit the present invention in any way, and is determined as needed by person conducting purification procedure.

EXAMPLES

Hereinafter, with reference to Examples, the present invention is described more specifically, but the present invention is in no way limited by these Examples. The conversion percentage of carbonyl compounds and the selectivity of corresponding alcohol compounds were calculated from values obtained in analysis by gas chromatography. The concentration unit ppm is all based on weight.

Example 1

5 g of E35S catalyst ($CuO/SiO_2$=67/27 in weight ratio) manufactured by JGC Catalysts and Chemicals Ltd., and 250 g of phenol containing 1800 ppm of hydroxyacetone (HA), 1300 ppm of α-phenylpropionaldehyde (α-PPA), 500 ppm of α-methylstyrene (α-MS), 6000 ppm of 2-phenyl-2-propanol (Cnol), 2.41 wt % of acetophenone (Anone) and other impurities were weighed, and introduced to a SUS 316 500-ml autoclave equipped with an electromagnetic induction rotating stirring device. The inside of the autoclave was purged with nitrogen (three times each at 0.9 MPa), and was purged with hydrogen (three times each at 0.9 MPa). The autoclave was filled with hydrogen at room temperature until the internal pressure reached 0.8 MPa, and was sealed. The autoclave was heated to 160° C. with stirring at a stirring rate of 450 rpm. Thereby, catalytic hydrogenation reaction was performed. Twelve hours thereafter, the heating was stopped. The autoclave was sufficiently cooled, and the inside of the autoclave was purged with nitrogen, and then the autoclave was opened. The content was filtered to remove the catalyst. Analysis of the resultant reaction liquid by gas chromatography found that HA conversion was 89.2%, α-PPA conversion was 99.3% and Anone conversion was 25.7%, and the corresponding alcohol compounds were obtained. Within the scope of analysis precision of gas chromatography, difference was not observed between before and after the reaction in terms of the concentration of dimers of α-methylstyrene (MSD), the concentration of the reaction product between phenol and α-MS, i.e., cumylphenol (CP), and the concentration of phenol. Results are shown in Table 1.

Examples 2 and 3

The reaction was performed in the same manner as Example 1, except that the catalyst used in Example 2 was G-22 catalyst ($CuO/Cr_2O_3/BaCrO_4/SiO_2$=50/35/10/5 in weight ratio) manufactured by Sud Chemie Catalyst, and the catalyst used in Example 3 was G-99 catalyst ($CuO/Cr_2O_3/BaCrO_4/MnO$=45/45/5/5 in weight ratio) manufactured by Sud Chemie Catalyst. Results are shown in Table 1.

Catalyst Preparation Example 1

Preparation of Catalyst Composed of Zinc Oxide and at Least One of Copper and Copper Oxide A solution prepared by dissolving 45.55 g of copper nitrate trihydrate and 54.90 g of zinc nitrate hexahydrate in 375 ml of distilled water was added to a solution prepared by dissolving 41.50 g of sodium carbonate in 375 ml of distilled water at room temperature with stirring, and the mixture solution was allowed to react for 2 hours. After the reaction, a precipitated reaction product was filtered and washed with distilled water. The resultant solid after the filtering and washing was collected, and dried at 110° C. for 5 hours, and then calcined in air at 400° C. for 5 hours. The obtained solid was a catalyst substantially composed of copper oxide and zinc oxide at a weight ratio of 1/1. The obtained catalyst was molded into a tablet-shape with 29R manufactured by Kikusui Seisakusho Ltd., to prepare a catalyst. This catalyst was used in a reaction.

Example 4

A fixed-bed reaction tube was filled with 100 ml of the molded catalyst obtained in Catalyst Preparation Example 1, and was charged with phenol containing 1800 ppm of hydroxyacetone (HA), 1300 ppm of α-phenylpropionaldehyde (α-PPA) 6000 ppm of 2-phenyl-2-propanol (Cnol), 2.41 wt % of acetophenone (Anone) and other impurities, and hydrogen under upflow conditions. Then, hydrogenation reaction was performed in the fixed-bed continuous reactor at a temperature of 160° C., at a pressure of 1.6 MPa, at a liquid hourly space velocity (LHSV) of 2 $hr^{-1}$, at a molar ratio of hydrogen/carbonyl compound of 20. The specimen for analysis was collected every hour, and was analyzed by gas chromatography. Results are shown in Table 1.

Example 5

The reaction was performed in the same manner as Example 4, except that the fixed-bed reaction tube was filled with 100 ml of E35S catalyst ($CuO/SiO_2$=67/27 in weight ratio) manufactured by JGS Catalysts and Chemicals Ltd., and the reaction temperature was 140° C. The specimen for analysis was collected every hour, and was analyzed by gas chromatography. Results are shown in Table 1.

TABLE 1

|  | Ex 1. | Ex. 2 | Ex. 3 | Ex. 4 | Ex. 5 |
|---|---|---|---|---|---|
| HA Conversion (%) | 89.2 | 100 | 100 | 96 | 99.9 |
| α-PPA Conversion (%) | 99.3 | 98.6 | 100 | 88.9 | 99.8 |
| Anone Conversion (%) | 25.7 | 50.2 | 91.9 | 16.3 | 91.4 |
| MSD concentration* (wt %) | 1.39 | 1.38 | 1.38 | 1.81 | 1.81 |
|  | 1.37 | 1.34 | 1.3 | 1.73 | 1.75 |
| CP concentration* (wt %) | 1.52 | 1.52 | 1.52 | 1.84 | 1.84 |
|  | 1.57 | 1.53 | 1.6 | 1.82 | 1.83 |
| PH concentration* (wt %) | 91.8 | 91.8 | 91.8 | 91.3 | 91.3 |
|  | 91.7 | 92 | 91.6 | 91.2 | 91.4 |

*Concentration of MSD, CP and PH: concentrations indicated in the upper side are values before hydrogenation, and concentrations indicated in the lower side are values after hydrogenation.

Comparative Example 1

5 g of a cation exchange resin (Amberlyst-15E), and 250 g of phenol containing 1800 ppm of hydroxyacetone (HA), 1300 ppm of α-phenylpropionaldehyde (α-PPA), 500 ppm of α-methylstyrene (α-MS), 6000 ppm of 2-phenyl-2-propanol (Cnol), 2.41 wt % of acetophenone (Anone) and other impurities were weighed, and introduced to a SUS 316 500-ml autoclave equipped with an electromagnetic induction rotating stirring device. The inside of the autoclave was purged with nitrogen (three times each at 0.5 MPa), and then the autoclave was sealed. The autoclave was heated to 110° C. with stirring at a stirring rate of 450 rpm. Thereby, the reaction was performed. Two hours thereafter, the heating was stopped, and the autoclave was sufficiently cooled and then opened. The content was filtered to remove the catalyst. Analysis of the resultant reaction liquid by gas chromatography found that HA conversion was 100%, α-PPA conversion was 100% and Anone conversion was 1%, but α-MS contained in the raw material and α-MS generated by dehydration reaction of Cnol, which are a useful component, reacted in their whole amount with phenol, to be converted to cumylphenol.

Comparative Example 2

The reaction was performed in the same manner as Comparative Example 1, except that in the Comparative Example 1, the cation exchange resin was replaced with a hydrogen exchange mordenite-type zeolite having an acidity function of Ho≤−8.2 and the reaction temperature was 160° C. As a result, it was found that HA conversion was 95%, α-PPA conversion was 92% and Anone conversion was 0%, but α-MS contained in the raw material and α-MS generated by dehydration reaction of Cnol, which are a useful component, reacted in their whole amount with phenol, to be converted to cumylphenol.

Example 6

7.5 g of a ShiftMax 210 catalyst (CuO/ZnO=42/47 in weight ratio) manufactured by Sud Chemie Catalyst, and 125 g of cumene were weighed, and introduced to a glass 300-ml flask equipped with a stirring device and a condenser. The flask was purged with nitrogen by feeding 500 ml/min of nitrogen gas thereto for 10 minutes. Thereafter, with stirring, the flask was heated in an oil bath to 140° C., and 100 ml/min of hydrogen gas was blown thereto at atmospheric pressure. Thereby, catalyst reduction treatment was performed for 5 hours. Thereafter, the flask was sufficiently cooled to collect cumene. Then, a 125 g of phenol containing 1.0 wt % of hydroxyacetone (HA) was weighed, and introduced to the flask having the catalyst. With stirring, the flask was heated in an oil bath to 80° C., and 100 ml/min of hydrogen gas was blown thereto at atmospheric pressure. Thereby, catalytic hydrogenation reaction was performed. Five hours thereafter, the heating was stopped. The flask was sufficiently cooled to collect a reaction liquid. Analysis of the reaction liquid by gas chromatography found that HA conversion was 14.3%, and cyclohexanol, which was a nuclear hydrogenation product of phenol, was given at not more than 10 ppm.

Comparative Example 3

7.5 g of a 2% palladium carbon beads catalyst manufactured by N.E. CHEMCAT CORPORATION, and 125 g of phenol containing 1.0 wt % of hydroxyacetone (HA) were weighed, and introduced to a glass 300-ml flask equipped with a stirring device and a condenser. With stirring, the flask was heated in an oil bath to 80° C., and 100 ml/min of hydrogen gas was blown thereto at atmospheric pressure. Thereby, catalytic hydrogenation reaction was performed. Five hours thereafter, the heating was stopped. The flask was sufficiently cooled to collect a reaction liquid. Analysis of the reaction liquid by gas chromatography found that HA conversion was 0.0%, which showed that no hydrogenation reaction of hydroxyacetone proceeded, and that cyclohexanol, which was a nuclear hydrogenation product of phenol, was given at 3000 ppm, which confirmed the loss of phenol, a useful component.

Comparative Example 4

The reaction was performed in the same manner as Comparative Example 3, except than 2.5 g of R-200L catalyst (bulk Raney nickel) manufactured by NIKKO RICA CORPORATION. Analysis by gas chromatography found that HA conversion was 10.0%, and that cyclohexanol, which was a nuclear hydrogenation product of phenol, was given at 1000 ppm, which confirmed the loss of phenol, a useful component.

Reference Example 1

The separability in distillation of hydroxyacetone (HA), a hydrogenated product of hydroxyacetone, i.e., propylene glycol (PG), and a hydrogenated product of α-phenylpropionaldehyde (α-PPA), i.e., 2-phenyl-1-propanol (PPnol), and phenol was studied in the following manner. A raw material prepared by adding HA, PG and PPnol each in an amount of 1000 ppm to phenol was subjected to fractional distillation using an Oldershaw glass distillation column with 30 trays. The distillation was performed at a raw material-feeding amount of 800 g, at a reflux ratio of 2, at a pressure of 200 Torr. The distillates were analyzed by gas chromatography, and analysis found that HA was detected in all the distillates, but PG and PPnol were detected in none of the distillates. Results are shown in FIG. 1.

What is claimed is:

1. A phenol purification process comprising bringing phenol into contact with a copper-based catalyst in the presence of hydrogen to convert carbonyl compound contained in the phenol to corresponding alcohol compound, and separating the alcohol compound and phenol by distillation.

2. The phenol purification process according to claim 1, wherein the carbonyl compound contained in the phenol is at least one compound selected from aromatic carbonyl compounds and aliphatic carbonyl compounds.

3. The phenol purification process according to claim 1, wherein the copper-based catalyst comprises at least one of copper and copper oxide (A) and oxide(s) of at least one element selected from silicon, aluminum, zinc, chromium, barium and manganese (B).

4. The phenol purification process according to claim 3, wherein the weight ratio (A)/(B) in the copper-based catalyst is in the range of from 9/1 to 1/9.

5. The phenol purification process according to claim 1, wherein the catalytic hydrogenation is performed at a reaction temperature of 50 to 300° C. at a hydrogen pressure of 0.5 to 30 MPa.

6. The phenol purification process according to claim 2, wherein the copper-based catalyst comprises at least one of copper and copper oxide (A) and oxide(s) of at least one element selected from silicon, aluminum, zinc, chromium, barium and manganese (B).

7. The phenol purification process according to claim 6, wherein the weight ratio (A)/(B) in the copper-based catalyst is in the range of from 9/1 to 1/9.

8. The phenol purification process according to claim 2, wherein the catalytic hydrogenation is performed at a reaction temperature of 50 to 300° C. at a hydrogen pressure of 0.5 to 30 MPa.

9. The phenol purification process according to claim 3, wherein the catalytic hydrogenation is performed at a reaction temperature of 50 to 300° C. at a hydrogen pressure of 0.5 to 30 MPa.

10. The phenol purification process according to claim 4, wherein the catalytic hydrogenation is performed at a reaction temperature of 50 to 300° C. at a hydrogen pressure of 0.5 to 30 MPa.

11. The phenol purification process according to claim 6, wherein the catalytic hydrogenation is performed at a reaction temperature of 50 to 300° C. at a hydrogen pressure of 0.5 to 30 MPa.

12. The phenol purification process according to claim 7, wherein the catalytic hydrogenation is performed at a reaction temperature of 50 to 300° C. at a hydrogen pressure of 0.5 to 30 MPa.

\* \* \* \* \*